United States Patent
Murray, III et al.

(10) Patent No.: US 11,612,505 B2
(45) Date of Patent: Mar. 28, 2023

(54) STENT GRAFT DELIVERY SYSTEM WITH OFFSET TAPERED TIP

(71) Applicant: Medtronic Vascular, Inc., Santa Rosa, CA (US)

(72) Inventors: Robert J. Murray, III, Santa Rosa, CA (US); Manthan Patel, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 157 days.

(21) Appl. No.: 16/862,720

(22) Filed: Apr. 30, 2020

(65) Prior Publication Data
US 2021/0338466 A1    Nov. 4, 2021

(51) Int. Cl.
*A61F 2/966* (2013.01)
*A61F 2/07* (2013.01)
*A61M 25/09* (2006.01)

(52) U.S. Cl.
CPC ............ *A61F 2/966* (2013.01); *A61F 2/07* (2013.01); *A61F 2/9661* (2020.05); *A61M 25/09* (2013.01)

(58) Field of Classification Search
CPC .......... A61F 2/966; A61F 2/07; A61F 2/9661; A61F 2002/9665; A61F 2002/061; A61F 2002/067; A61F 2/954; A61F 2/95; A61F 2002/9511; A61M 25/09; A61M 25/0032; A61M 2025/0081; A61M 25/0071
See application file for complete search history.

(56) References Cited

U.S. PATENT DOCUMENTS

| 6,999,809 B2 | 2/2006 | Currier et al. | |
| 2004/0230287 A1* | 11/2004 | Hartley | A61F 2/954 606/108 |
| 2008/0039863 A1 | 2/2008 | Keegan et al. | |
| 2008/0167704 A1* | 7/2008 | Wright | A61F 2/954 623/1.23 |

(Continued)

FOREIGN PATENT DOCUMENTS

| EP | 1399095 | 3/2004 | |
| EP | 2036519 A1 * | 3/2009 | A61F 2/954 |

(Continued)

OTHER PUBLICATIONS

Partial European Search Report for European Application No. 21170191.7, completed Sep. 16, 2021, 13 pages.

(Continued)

*Primary Examiner* — Kelly J Bekker
*Assistant Examiner* — Andrew P. Restaino
(74) *Attorney, Agent, or Firm* — Brooks Kushman P.C.

(57) ABSTRACT

A stent graft delivery system and method of assembling the same is disclosed. The stent graft delivery system includes a stent graft cover configured to maintain a stent graft in a constricted configuration, and is configured to slide relative to the stent graft to enable the stent graft to expand radially outwardly. The stent graft cover extends along a first central axis. A tapered tip defining an opening therethrough is configured to track along a guidewire. The opening extends along a second central axis that is offset from the first central axis. This provides a delivery system with an opening in a leading edge that is not center relative to the outer stent graft cover.

14 Claims, 5 Drawing Sheets

(56) References Cited

U.S. PATENT DOCUMENTS

| | | | |
|---|---|---|---|
| 2008/0269794 A1* | 10/2008 | Spurchise | A61B 17/0057 |
| | | | 606/191 |
| 2010/0262217 A1* | 10/2010 | Bruszewski | A61F 2/966 |
| | | | 623/1.13 |
| 2011/0257720 A1 | 10/2011 | Peterson et al. | |
| 2012/0143305 A1* | 6/2012 | Berra | A61F 2/844 |
| | | | 623/1.13 |
| 2013/0274860 A1 | 10/2013 | Argentine | |
| 2015/0272759 A1 | 10/2015 | Argentine | |
| 2017/0000606 A1* | 1/2017 | Crisostomo | A61F 2/2436 |
| 2018/0177622 A1* | 6/2018 | Chu | A61M 39/105 |
| 2019/0133756 A1* | 5/2019 | Zhang | A61F 2/2418 |

FOREIGN PATENT DOCUMENTS

| | | |
|---|---|---|
| EP | 1399095 B1 | 6/2017 |
| WO | 03/002033 A1 | 1/2003 |

OTHER PUBLICATIONS

Extended European Search Report for European Application No. 21170191.7, completed Jan. 5, 2022, 15 pages.

\* cited by examiner

STENT GRAFT DELIVERY SYSTEM WITH OFFSET TAPERED TIP

TECHNICAL FIELD

The present disclosure relates to a delivery system for a stent graft, for example a branched stent graft. In embodiments, the present disclosure relates to such a branched stent graft delivery system having an offset tapered tip.

BACKGROUND

The use of endovascular procedures has been established as a minimally invasive technique to deliver a variety of clinical treatments in a patient's vasculature. A stent graft is an implantable device made of a tube-shaped surgical graft covering and an expanding or self-expanding metal frame. The stent graft is placed inside a blood vessel to bridge, for example, an aneurismal, dissected, or other diseased segment of the blood vessel, and, thereby, exclude the hemodynamic pressures of blood flow from the diseased segment of a blood vessel such as the aorta.

Depending on the region of the aorta involved, the aneurysm may extend into areas having vessel bifurcations or segments of the aorta from which smaller "branch" arteries extend. For example, thoracic aortic aneurysms can include aneurysms present in the ascending thoracic aorta, the aortic arch, and/or branch arteries that emanate therefrom, such as subclavian or left or right common carotid arteries. In some cases, a branched stent graft can be used to treat such aneurysms. For example, a main stent graft can be deployed in the main vessel (e.g., aortic arch), and a supplemental, secondary stent graft can be deployed in the branched artery (e.g., left subclavian).

SUMMARY

According to one embodiment, a stent graft delivery system comprises a stent graft cover and a tapered tip. The stent graft cover is configured to maintain a stent graft in a constricted configuration, and configured to slide relative to the stent graft to enable the stent graft to expand radially outwardly, wherein the stent graft cover extends along a first central axis. The tapered tip defines an opening therethrough that is configured to track along a guidewire, wherein the opening extends along a second central axis that is offset from the first central axis.

According to another embodiment, a stent graft delivery system comprises a stent graft cover, a tapered tip, a tip capture mechanism, and a spindle. The stent graft cover is configured to maintain a stent graft in a constricted configuration, and configured to slide relative to the stent graft to enable the stent graft to expand radially outwardly. The tapered tip defines an opening therethrough that is configured to track along a guidewire. The tip capture mechanism has an inner member aligned with the opening, and the inner member has an inner lumen secured to the tapered tip and an outer lumen disposed about the inner lumen and configured to slide along an outer surface of the inner lumen. The spindle is aligned with the opening and has an inner surface contacting the inner lumen and an outer surface contacting the tapered tip to secure the tapered tip to the inner lumen.

According to another embodiment, a method of assembling a stent graft delivery system comprises fitting a barbed spindle about an outer surface of an inner lumen of an inner member, wherein the barbed spindle defines an opening extending about a central axis; press-fitting a tapered tip about an outer surface of the barbed spindle, wherein the tapered tip includes an opening extending about the central axis when press-fitted to the barbed spindle; and assembling a stent graft cover about a portion of the tapered tip such that a central axis of the stent graft cover is offset from the central axis of the opening of the barbed spindle.

DETAILED DESCRIPTION

Figure 1:
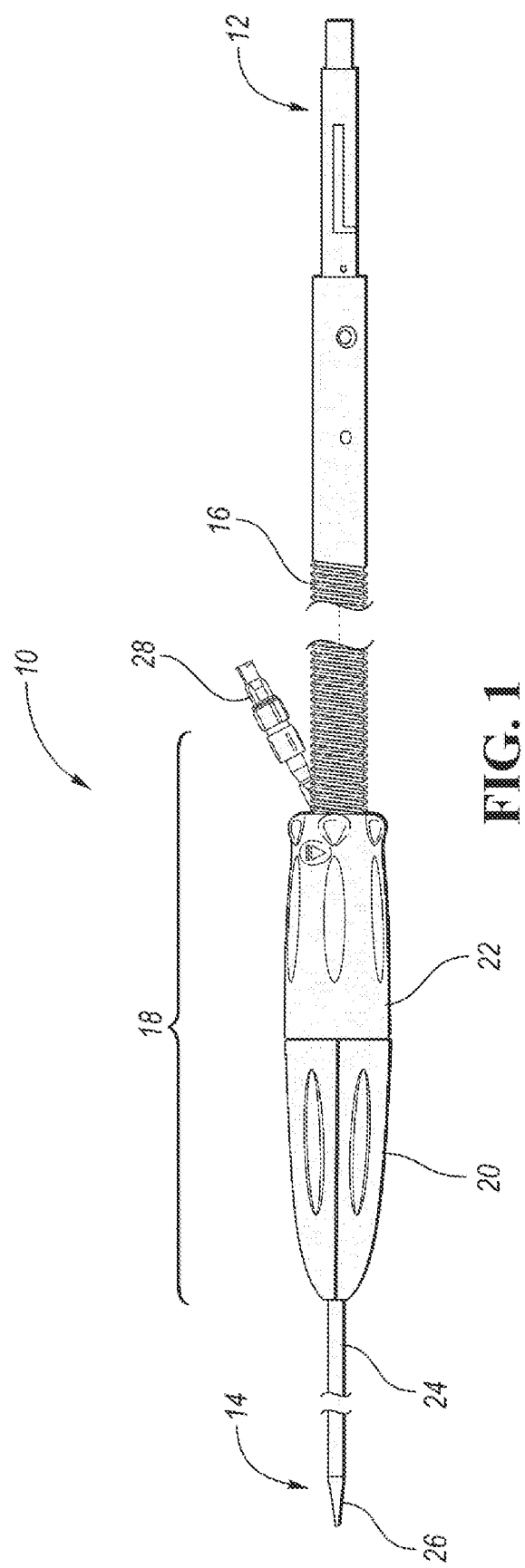
FIG. 1 is a schematic illustration of a stent graft delivery system, according to one embodiment.
Figure 2:
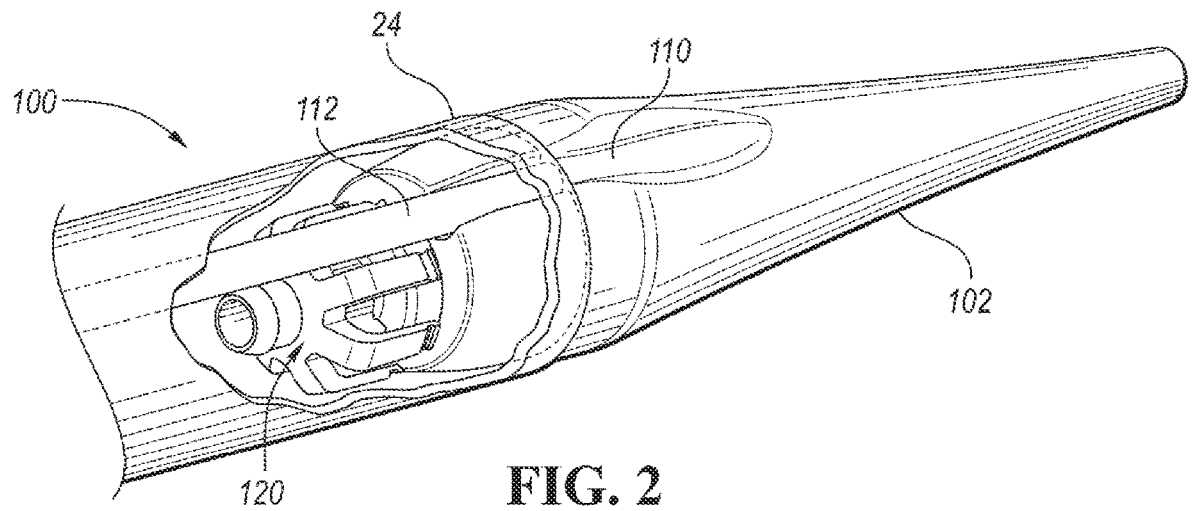
FIG. 2 is a rear perspective view of a distal end of the delivery system with an inner member removed and a stent graft cover partially transparent for view of the inner components, according to one embodiment.
Figure 3:
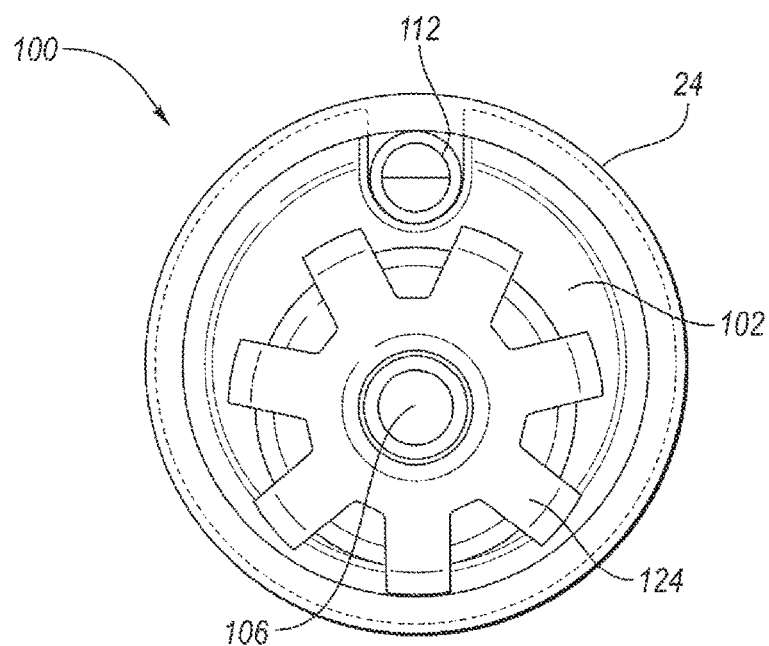
FIG. 3 is a rear view of the distal end of the delivery system from inside the delivery system, according to one embodiment.

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the embodiments. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Directional terms used herein are made with reference to the views and orientations shown in the exemplary figures. A central axis is shown in the figures and described below. Terms such as "outer" and "inner" are relative to the central axis. For example, an "outer" surface means that the surfaces faces away from the central axis, or is outboard of another "inner" surface. Terms such as "radial," "diameter," "circumference," etc. also are relative to the central axis. The terms "front," "rear," "upper" and "lower" designate directions in the drawings to which reference is made.

Unless otherwise indicated, for the delivery system the terms "distal" and "proximal" are used in the following description with respect to a position or direction relative to a treating clinician. "Distal" and "distally" are positions distant from or in a direction away from the clinician, and "proximal" and "proximally" are positions near or in a direction toward the clinician. For the stent-graft prosthesis, "proximal" is the portion nearer the heart by way of blood flow path while "distal" is the portion of the stent-graft further from the heart by way of blood flow path.

The following detailed description is merely exemplary in nature and is not intended to limit the invention or the application and uses of the invention. Although the description is in the context of treatment of blood vessels such as the aorta, coronary, carotid and renal arteries, the invention may also be used in any other body passageways where it is deemed useful.

Thoracic aortic aneurysms with disease progression extending into the aortic arch can be treated with a branched stent graft and delivery system. Branched stent graft delivery systems can be used to deliver and deploy stent grafts that are configured to couple with secondary stent grafts that extend into vessels or "branches" within a patient's vasculature, such as the thoracic aorta. For example, during a surgical procedure, a main guidewire may be fed into the vasculature and into a main vessel (e.g., aortic arch), and a secondary guidewire may be fed into a secondary vessel or branched artery (e.g., left subclavian). The stent graft delivery system can include a main lumen that tracks along the main guidewire, and a secondary lumen that tracks along the secondary guidewire. A main stent graft can be deployed in a main vessel, and a supplemental, secondary stent graft can be deployed in the branched artery. An example of such a surgical procedure is described in U.S. patent application Ser. No. 16/828,644 titled Branched Stent Graft Delivery System, which is hereby incorporated by reference.

FIG. 1 shows a branched stent graft delivery system 10 according to one embodiment. The branched stent graft delivery system 10, also more simply referred to as a stent graft delivery system or a delivery system, includes an endovascular catheter and extends between a proximal end 12 and a distal end 14. The terms "proximal end" and "distal end" are not intended to be limiting, as a surgical clinician may, during a procedure, in fact be located closer to the distal end 14 than the proximal end 12. Therefore, the proximal end and the distal end may be referred to as a "first end" and a "second end," respectively.

A threaded screw gear 16 extends along an axis between the proximal end 12 and the distal end 14. The threaded screw gear may be a multi-part shell configured to connect together to make a tubular screw gear. In one embodiment, the screw gear 16 is two half-shells configured to connect (e.g., snap or assemble) together.

A handle assembly 18 is provided for grip by the clinician. The handle assembly 18 may include two separable portions, namely a front grip 20 and an external slider 22. The front grip 20 may be fixed relative to the screw gear 16, and the external slider 22 may rotate about a threaded outer surface of the screw gear 16 to move linearly along the screw gear 16. For example, during deployment of a stent graft, the external slider 22 is rotated to move toward the proximal end 12. Since the external slider 22 is operatively coupled to a stent graft cover 24 surrounding the stent graft, the stent graft cover 24 is retracted with the linear movement of the external slider 22. Meanwhile, a tip 26 at the distal end 14 of the delivery system 10, which has openings to track over the guidewires, can remain steady within the vessel as the stent graft cover 24 is retracted away from the tip 26. Retraction of the stent graft cover 24 allows the stent graft to expand within the patient's vessel. Once the stent graft is deployed, the entire stent graft delivery system 10 may be retracted from the patent's vessel.

The stent graft can be self-expanding, in that it includes structures that are shaped or formed from a material that can be provided with a mechanical memory to return the structure from a compressed or constricted delivery configuration to an expanded deployed configuration. The stent graft can include two main components: a tubular graft, and one or more stents for supporting and expanding the graft. The graft may be formed from any suitable graft material, for example and not limited to, a low-porosity woven or knit polyester, DACRON material, expanded polytetrafluoroethylene, polyurethane, silicone, or other suitable materials. In another embodiment, the graft material can also be a natural material such as pericardium or another membranous tissue such as intestinal submucosa. The stent is radially-compressible and expandable, is coupled to the graft material for supporting the graft material, and is operable to self-expand into apposition with the interior wall of a body vessel (not shown). Each stent can be constructed from a self-expanding or spring material, such as but not limited to Nitinol, stainless steel, a pseudo-elastic metal such as a nickel titanium alloy or nitinol, various polymers, or a so-called super alloy, which may have a base metal of nickel, cobalt, chromium, or other metal, or other suitable material. This allows the stent graft to expand when the stent graft cover 24 is retracted therefrom. The stent may be a sinusoidal patterned ring including a plurality of crowns or bends and a plurality of struts or straight segments with each crown being formed between a pair of opposing struts.

While the screw gear 16 is illustrated and described herein as having a threaded outer surface, it should be understood that in other embodiments, the screw gear is not threaded, the external slider 22 can slide linearly along the screw gear, or any other suitable mechanism may be used to retract the graft cover.

The stent graft delivery system 10 may also include an access port 28. The access port 28 provides an opening for insertion, removal, or receiving of a secondary guidewire lumen, or branching lumen, for surrounding a secondary guidewire. The delivery system 10 can track along both the main guidewire and the secondary guidewire during delivery of the stent graft.

FIGS. 2-5 illustrate various views of internal components of a distal end 100 of a stent graft delivery system, such as that illustrated in FIG. 1. In other words, the structure shown in FIGS. 2-5 and described below can be substituted for the distal end 14 of FIG. 1.

The distal end 100 includes a tip 102, also referred to as a tapered tip due to its tapered profile. The tapered tip 102 provides a leading edge of the delivery system 10, and tracks over one or more guidewires. In particular, the tapered tip 102 includes a leading edge or front surface 104 that defines a cut-out or opening 106 configured to receive a main guidewire. The opening 106 can be an aperture in the material of the tapered tip 102 with an inner surface of the tapered tip 102 surrounding the main guidewire. The opening 106 is aligned with an inner member 108 within the stent graft cover 24, as will be described below.

The tapered tip 102 can also include a second opening 110 configured to receive a secondary guidewire. This second opening 110 allows the delivery system 10 to track over the secondary guidewire simultaneously with the main guidewire. The second opening 110 is aligned with a secondary lumen 112 within the stent graft cover 24, as will be described below.

The stent graft cover 24 is the outer-most sheath or lumen of the stent graft delivery system. The stent graft cover initially contains or surrounds a proximal portion of the tapered tip 102, as well as the inner member 108, the secondary lumen 112, and a stent graft (not shown). As explained above, after insertion of the delivery system 10 to a desired location within the patient's vasculature, the surgical technician may utilize the handle to retract the stent graft cover 24, allowing the stent graft to deploy. The stent graft cover 24 is an elongate tubular member defining a lumen from a proximal end to a distal end thereof. The stent graft cover 24 may be formed from a plurality of different materials or combination of materials; in one embodiment, the stent graft cover 24 is formed with a braided stainless steel wire with a flat or rounded cross section that is sandwiched between layers of PEBAX® or VESTAMID®.

The inner member 108 defines a hollow lumen, and can be two parts. For example, the inner member 108 can include an inner lumen or guidewire lumen 114, and an outer lumen or capture lumen 116. Each of the guidewire lumen 114 and the capture lumen 116 may be made from a high tensile polymer, such as polyether ether ketone (PEEK) or a polyimide. The capture lumen 116 is larger than the guidewire lumen 114 and receives the guidewire lumen 114 therein. The guidewire lumen 114 may be fixed to the tapered tip 102, while the capture lumen 116 may be slideable along the outer surface of the guidewire lumen to slide toward the proximal end of the delivery system 10. The guidewire lumen 114 may be fixed in alignment with the opening 106 of the tapered tip 102 to receive the main guidewire therethrough and track along the main guidewire during insertion into the patient.

The delivery system also includes a tip capture mechanism, shown generally at 120. The tip capture mechanism 120 is coupled to, and actuated by, the inner member 108. In particular, according to the illustrated embodiment, the tip capture mechanism 120 includes a capture fitting 122 having a plurality of fingers 124 or prongs. The capture fitting 122 is configured to hold a stent, ring, loop, or other such structure of a proximal end of the stent graft. This allows the stent graft to be deployed (e.g., when the stent graft cover 24 is retracted) while its proximal end is held in a constricted manner during deployment. A proximal end of the capture fitting 122 is fixed to the capture lumen 116 to move with the capture lumen 116. Once the stent graft is at least partially deployed, the capture lumen 116 can be slid toward the surgical technician relative to the guidewire lumen 114, thereby releasing the fingers 124 of the tip capture fitting 122 from the stent, ring, loop, or the like of the stent graft. This releases the stent graft from the delivery system, and the entire catheter can then be removed from the patient. While one example of a tip capture mechanism has been described, any tip capture mechanism may be compatible with the present disclosure. For example, the tip capture mechanism may be configured such that the inner tube extends axially forward to move the tip forward relative to the outer tube and spindle, thereby releasing the stent graft. Other tip capture mechanisms may include a single tube, three or more tubes, or other systems.

The secondary lumen 112 is also provided within the stent graft cover 24. The secondary lumen 112 is aligned with the opening 110 to receive the secondary guidewire therethrough, and track along the secondary guidewire during insertion into the patient's vasculature. The secondary lumen may be located radially outboard of the inner member 108, but radially inward of the stent graft cover 24.

In previous designs of stent graft delivery systems, the addition of a secondary lumen within the confines of the stent graft could present several issues. For example, packaging constraints within the delivery system would be compromised, requiring other components within the confines of the stent graft to be reduced in size while still maintaining feasibility. Moreover, a bulge could be created in the stent graft cover as the secondary lumen is bent around the stent graft components. Such a bulge can make the profile of the delivery system lager than the intended outer profile. There is also difficulty in maintaining alignment of the secondary lumen and the inner components. In many cases, the secondary lumen is forced to bend around the arms of the capture mechanism and can become bent or misshapen in a way that could compromise the lumen patency or at least increase wire friction through the lumen.

Therefore, according to various embodiments described herein, the tapered tip 102 is designed to allow for smaller components within the confines of the stent graft cover 24. In embodiments, the front surface 104 and the opening 106 at the distal end of the tapered tip 102 is not concentric with the stent graft cover 24. This allows other components of the delivery system, such as the inner member 108 and tip capture mechanism 120, to also assume a location that is not concentric with the stent graft cover 24. These components can be offset from center in a direction away from the secondary lumen 112, giving more space for the secondary lumen 112 to assume and not be bent or create a bulge in the stent graft cover 24. Also, this allows an easier retraction of the secondary lumen 112, if necessary, during a surgical deployment prior to retraction of the stent graft cover 24.

Figure 4:
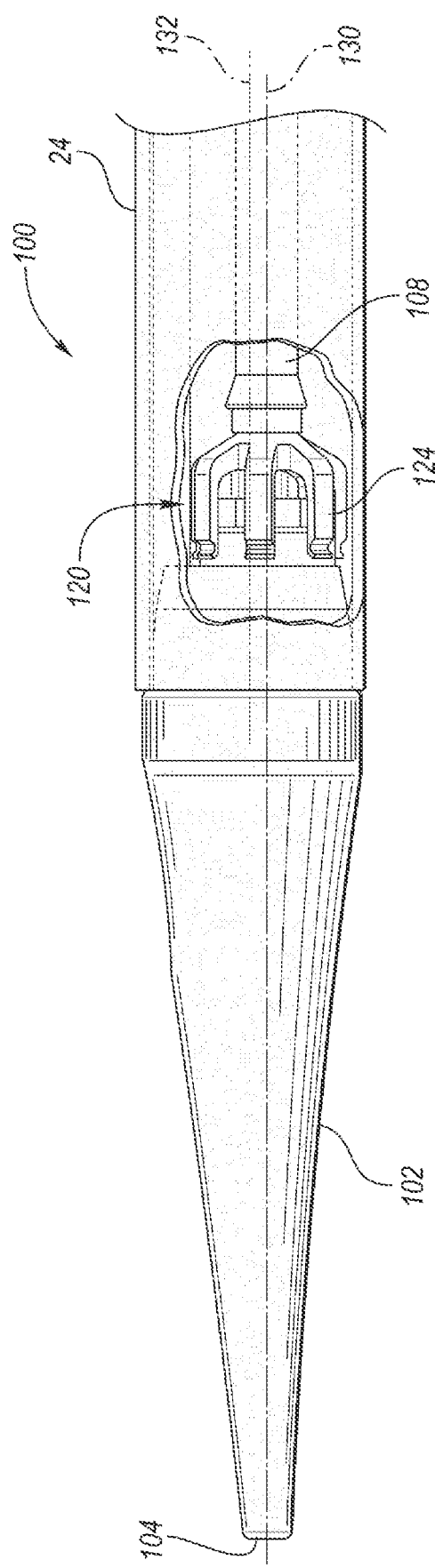
FIG. 4 is a side elevation view of the distal end of the delivery system with an opening in the stent graft cover for view of the inner components, according to one embodiment.
Figure 5:
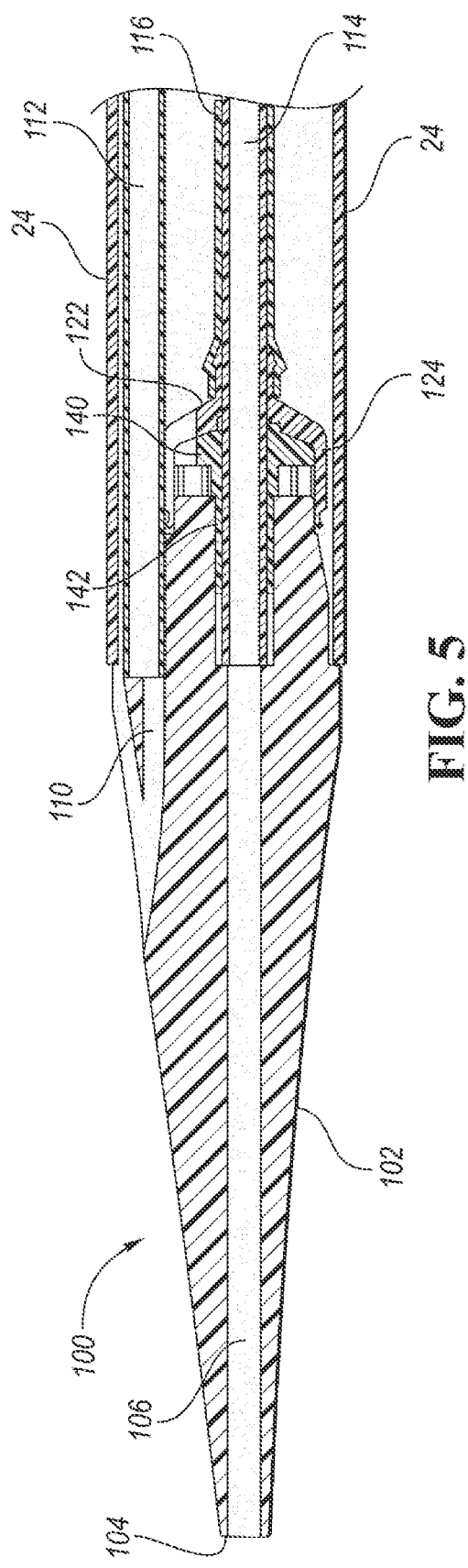
FIG. 5 is a cross-sectional view of the distal end of the delivery system, according to one embodiment.

The nature of the offset can be seen in the FIGS. 4 and 5, and in particular FIG. 4. The distal surface or front surface 104, the opening 106, the inner member 108, and the tip capture mechanism 120 are all concentric and have a common first central axis 130. Meanwhile, the stent graft cover 24 has a second central axis 132 that is offset from the first central axis 130. The secondary lumen 112 is positioned toward the perimeter (e.g., touching or adjacent) of the stent graft cover 24. The first central axis 130 is located away from the second central axis 132 in a direction away from the second central axis 132. While the terms "first" and "second" are used herein, it should be understood that these terms are used merely to delineate and label the two components separately, and the terms can be interchangeable.

To accommodate for this offset-axis relationship, the internal components may be reduced in size. For example, the tip capture mechanism 120 may be reduced in size, to allow the components to be offset from their original, central positioning. This creates more space for the secondary lumen 112.

This also allows for the tapered tip 102 to be assembled to (e.g., pressed into) the delivery system late in the assembly process, in which the tapered tip 102 can be precisely positioned, rotationally, to optimize engagement with the secondary lumen 112. In other words, once the secondary lumen 112 is assembled and in place within the stent graft cover 24, the tapered tip 102 can be assembled to the remainder of the delivery system at a rotational alignment such that the opening 110 is aligned with the secondary lumen 112.

To facilitate attachment during assembly, a spindle 140 is provided. The spindle 140 is a barbed insert for attachment of the tapered tip 102 to the inner member 108. The spindle 140 is shown in the cross-sectional view in FIG. 5, in isolation in FIG. 6 and attached about the guidewire lumen 114 in FIG. 7. The spindle 140 is configured to align with the tip capture device 120 along the first central axis 130 to hold the stent graft in place during delivery (e.g., the stent apices may be held between the spindle 140 and the capture fitting 122). The spindle 140 is fixed to the tapered tip 102, and does not move with the capture lumen 116 or stent graft cover 24 during deployment of the stent graft. In previous designs, a spindle was overmolded onto a tapered tip, but this can create difficulty with non-concentric arrangements. Instead, in embodiments herein the spindle 140 is a separate component and separately assembled to the tapered tip 102.

In one embodiment, a portion of the delivery system may be pre-assembled or pre-loaded such that the tapered tip 102 may be assembled to the guidewire lumen 114, which is inserted into the capture lumen 116, and the tapered tip 102 is pressed onto the spindle 140. This eliminates a need for any threaded screw fit, and instead provides a simple press-fit attachment between the tapered tip 102 and the spindle 140. The tapered tip 102 may be formed to include an inner surface 142 that creates a widened portion of the opening 106 at a proximal end of the tapered tip 102. The inner surface 142 of the widened opening can be pressed around and fit about an exterior surface 144 of the spindle 140.

Figure 6:
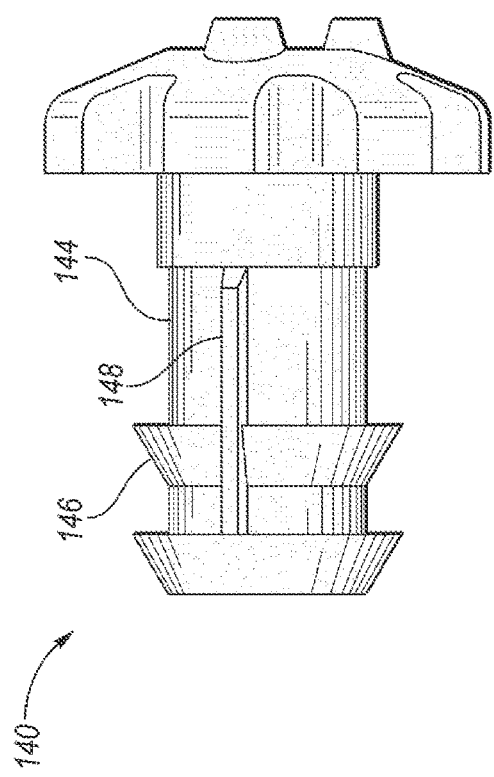
FIG. 6 is a side view of a spindle configured to be positioned within the distal end of the delivery system, according to one embodiment.
Figure 7:
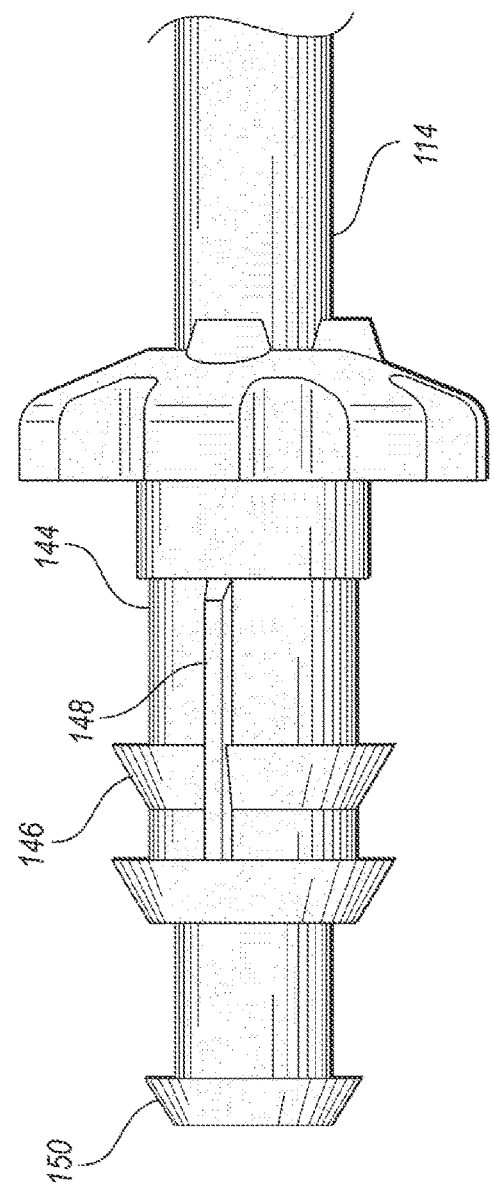
FIG. 7 is a side view of the spindle of FIG. 6 placed about an inner member of the delivery system, according to one embodiment.

To facilitate the press-fit attachment, the exterior surface 144 of the spindle 140 may be provided with surface features configured to inhibit movement. In particular, the exterior surface 144 can include a first set of barbs 146 and a second set of barbs 148. The first set of barbs 146 may include one or more fins, projections, or the like that extend annularly about the first central axis 130. As can be seen in FIGS. 6-7, these barbs 146 may be formed to be angled such that a proximal end of the barbs 146 extends further radially outward compared to a distal end of the barb 146. This angle inhibits the tapered tip 102 from pulling away from the spindle 140 after assembly. The barbs 146 may be flattened or otherwise compressed once the tapered tip 102 is pressed over the barbs 146.

The second set of barbs 148 may include one or more circumferentially-spaced fins each extending in an axial direction along the exterior surface 144. These barbs 148 are configured to inhibit rotation between the tapered tip 102 and the spindle 140.

To facilitate the press-fit attachment between the guidewire lumen 114 and the tapered tip 102, the exterior surface of the guidewire lumen 114 may be provided with one or more barbs 150. The barbs 150 may be similar to the first set of barbs 146, being disposed annularly about the first central axis 130. While not shown, the guidewire lumen 114 may also be provided with one or more barb that is similar in design to the second set of barbs 148.

As can be seen in FIGS. 4 and 5, the offset-axis relationship of the delivery system can yield a tapered tip with varying thicknesses of material. For example, referring to FIG. 5, the tapered tip 102 has a thicker amount of material above the opening 106 than below. Said another way, there is more material of the tapered tip on the side of the first central axis 130 closer to the second opening 110 than the other side of the first central axis 130. The first central axis 130 is not the centerline of the taper of the tapered tip 102.

Figure 8:
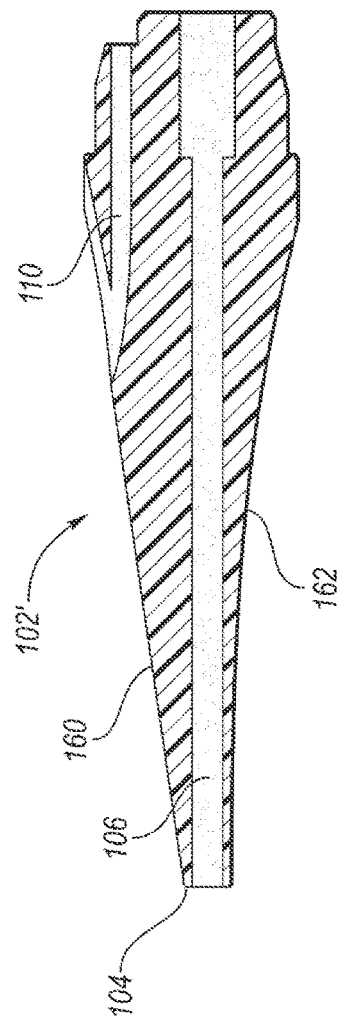
FIG. 8 is a cross-sectional view of the tapered tip of the delivery system having a profile according to one embodiment.
Figure 9:
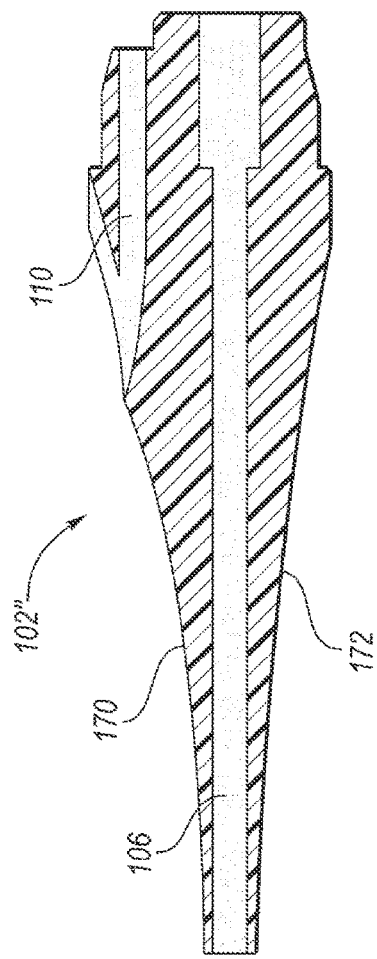
FIG. 9 is a cross-sectional view of the tapered tip of the delivery system having a profile according to another embodiment.
Figure 10:
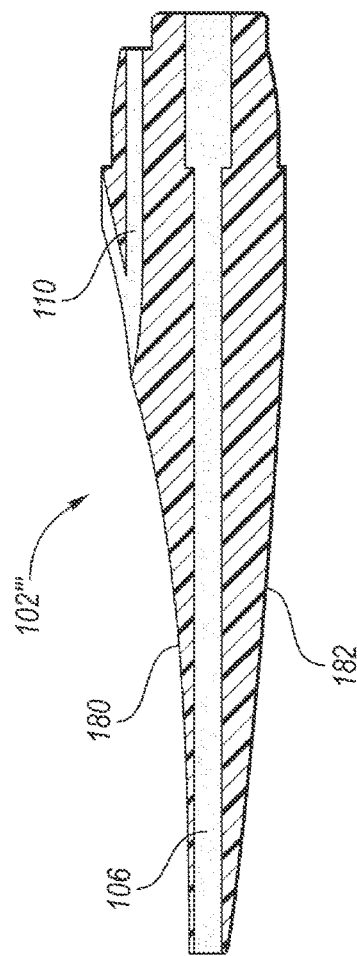
FIG. 10 is a cross-sectional view of the tapered tip of the delivery system having a profile according to another embodiment.

FIGS. 8-10 illustrate various embodiments for varying the thickness of the tapered tip on either side of the opening 106. Varying the shape or thickness of the tapered tip 102 can provide a preferential bending direction during insertion into the vasculature.

The tapered tips of FIGS. 8-10 include the structure of the tapered tip 102 described above, unless described otherwise. FIG. 8 shows a tapered tip 102' according to one embodiment. The tapered tip 102' has a first portion 160 on the side of the opening 106 closer to the second opening 110, and a second portion 162 on the side of the opening 106 away from the second opening 110. The first portion 160 is generally conical in shape, generally constantly increasing in thickness (e.g., between the opening 106 and the outer surface) from the front surface 104 toward the rear. The outer surface of the first portion 160 is generally linear. Meanwhile, the second portion 162 has an outer surface that is concave. Therefore, the second portion 162 is not generally conical in shape, as the thickness of the second portion is not constant. This can influence the tracking performance of the delivery system in a first manner, with a first preferred bending direction that may allow for easier tracking and device placement.

FIG. 9 shows a tapered tip 102" according to another embodiment. The tapered tip 102" has a first portion 170 on the side of the opening 106 closer to the second opening 110, and a second portion 172 on the side of the opening 106 away from the second opening 110. The first portion 170 has an outer surface that is generally concave, and the second portion 172 has an outer surface that is generally concave. The outer surfaces of the two portions 170, 172 can be pitched or concave at different degrees of magnitude. For example, the second portion 172 can be more concave than the first portion 170. Moreover, the outer surfaces of both the first and second portions 170, 172 can be angled such that the thickness of both portions is equal or substantially similar for at least a majority of the length of the portions 170, 172. This can influence the tracking performance of the delivery system in another manner, with another preferred bending direction that may allow for easier tracking and device placement.

FIG. 10 shows a tapered tip 102'" according to another embodiment. The tapered tip 102'" has a first portion 180 on the side of the opening 106 closer to the second opening 110, and a second portion 182 on the side of the opening 106 away from the second opening 110. The second portion 182 may have an outer surface that is generally linear, creating a conical shape of the second portion 182. Meanwhile, the outer surface of the first portion 170 may be concave. Opposite to the embodiment of FIG. 8, in this embodiment, the thickness of the second portion 182 may exceed the thickness of the first portion 180 for at least a majority of the length of the portions 180, 182. This can influence the tracking performance of the delivery system in another manner, with another preferred bending direction that may allow for easier tracking and device placement.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, to the extent any embodiments are described as less desirable than other embodiments or prior art implementations with respect to one or more characteristics, these embodiments are not outside the scope of the disclosure and can be desirable for particular applications.

What is claimed is:

1. A stent graft delivery system comprising:
a stent graft cover configured to maintain a stent graft in a constricted configuration, and configured to slide relative to the stent graft to enable the stent graft to expand radially outwardly, wherein the stent graft cover extends along a first central axis;
a tapered tip defining a first opening extending within the tapered tip and configured to track along a first guidewire and a second opening extending within the tapered tip and configured to track along a second guidewire, wherein the first opening extends along a first offset axis offset from the first central axis; and
a tip capture mechanism proximal of the tapered tip and configured to engage the stent graft,
wherein the tapered tip includes a front surface at a leading edge of the stent graft delivery system, wherein the first opening is centered with respect to the front surface.

2. The stent graft delivery system of claim 1, wherein the second opening extends along a second offset axis offset from the first offset axis and the first central axis, the tapered tip includes a cross section including the first and second offset axes, the cross section includes a first side above the first opening and a second side below the first opening.

3. The stent graft delivery system of claim 2, wherein the first side is thicker than the second side.

4. The stent graft delivery system of claim 1, further comprising a secondary lumen disposed within the stent graft cover and aligned with the second opening to receive the second guidewire therethrough.

5. The stent graft delivery system of claim 1, the tip capture mechanism further comprising an inner member and a plurality of fingers configured to engage the stent graft, wherein the inner member extends along the first offset second central axis.

6. The stent graft delivery system of claim 5, wherein the inner member includes an inner lumen fixed to the tapered tip, and an outer lumen configured to slide relative to the inner lumen.

7. The stent graft delivery system of claim 6, further comprising a spindle disposed about a portion of the inner lumen and press-fit into the first opening of the tapered tip.

8. The stent graft delivery system of claim 7, wherein the spindle includes a plurality of barbs extending radially outward therefrom, wherein the barbs are configured to inhibit relative movement between the tapered tip and the spindle.

9. A stent graft delivery system comprising:
a stent graft cover configured to maintain a stent graft in a constricted configuration, and configured to slide relative to the stent graft to enable the stent graft to expand radially outwardly, wherein the stent graft cover extends along a first axis;
a tapered tip at a distal most end of the delivery system defining a first opening extending within the tapered tip and configured to track along a first guidewire and a second opening extending within the tapered tip and configured to track along a second guidewire, wherein the first opening extends along a first offset axis offset from the first axis;
a tip capture mechanism proximal of the tapered tip and having an inner member that extends along the first offset axis, the inner member having an inner lumen secured to the tapered tip and an outer lumen disposed about the inner lumen and configured to slide along an outer surface of the inner lumen; and
a spindle aligned with the first opening and having an inner surface contacting the inner lumen and an outer surface contacting the tapered tip to secure the tapered tip to the inner lumen.

10. The stent graft delivery system of claim 9, wherein the spindle is press-fit between the inner lumen and the tapered tip.

11. The stent graft delivery system of claim 9, wherein the spindle has a plurality of surface features on an exterior surface thereof that are configured to inhibit relative movement between the spindle and the tapered tip.

12. The stent graft delivery system of claim 11, wherein the surface features include one or more annular barbs extending about the first axis thereof and configured to inhibit translational movement between the tapered tip and the spindle.

13. The stent graft delivery system of claim 11, wherein the surface features include one or more axially-extending barbs circumferentially spaced about the first axis thereof and configured to inhibit rotational movement between the tapered tip and the spindle.

14. The stent graft delivery system of claim 11, wherein the inner lumen includes one or more barbs extending radially outwardly from an exterior surface thereof, wherein the one or more barbs are configured to inhibit translational movement between the tapered tip and the inner lumen.

* * * * *